United States Patent [19]

Leto

[11] Patent Number: 5,182,262
[45] Date of Patent: Jan. 26, 1993

[54] CALMODULIN BINDING PEPTIDE DERIVATIVES OF NON-ERYTHROID ALPHA SPECTRIN

[75] Inventor: Thomas Leto, Washington, D.C.

[73] Assignee: The United States of America as represented by the Department of Health and Human Services, Washington, D.C.

[21] Appl. No.: 318,172

[22] Filed: Mar. 2, 1989

[51] Int. Cl.$^5$ .................. A61K 37/00; A61K 37/02; C07K 5/00; C07K 7/00
[52] U.S. Cl. ........................ 514/13; 514/12; 514/14; 530/324; 530/325; 530/326
[58] Field of Search ................... 514/13, 14, 12; 530/325, 326, 350, 387, 324

[56] References Cited

PUBLICATIONS

Speicher et al., Nature, vol. 311, 1984, pp. 177–180.
Glenney et al., Proc. Natl. Acad. Sci., vol. 79, 1982, pp. 4002–4005.
Leto et al., Mol. Cell Biol., vol. 8, No. 1, 1988, pp. 1–9.
Sahr et al., J. Biol. Chem., vol. 265, No. 8, 1990, pp. 4434–4443.
Leto et al., Biol. Abstr., vol. 87 (12), Rf. No. 122170.
Moon et al., J. Biol. Chem., vol. 265, No. 8, 1990, pp. 4427–4433.
Birkenmeier et al., Proc. Natl. Acad. Sci., vol. 82, 1985, pp. 5671–5675.

Primary Examiner—Merrell C. Cashion, Jr.
Assistant Examiner—Avis M. Davenport
Attorney, Agent, or Firm—Birch, Stewart, Kolasch & Birch

[57] ABSTRACT

The present invention relates to a polypeptide and derivatives thereof deduced from the native structure of non-erythroid alpha spectrin and compositions thereof. One embodiment of the invention is 24 amino acids in length and composed of the following linear sequence of residues: Lys-Thr-Ala-Ser-Pro-Trp-Lys-Ser-Ala-Arg-Leu- Met-Val-His-Thr-Val-Ala-Thr-Phe-Asn-Ser-Ile-Lys-Glu. The invention further relates to methods of using the polypeptide, such as methods for treating disorders including prophylaxis against organ and tissue transplant rejection or treatment of autoimmune disorders.

30 Claims, 6 Drawing Sheets

FIG. 2

```
NON-ERYTH  IALRQEIDNQYHSLLELGEKRKGMLEKSCKKFMLFREANELQQWINEKEAALTSEEVGADLEQVEVLQKK    REPEAT
           ||||| ||| ||| |  | ||  |   ||   ||| ||  ||||  ||   ||||   ||| ||        11
ERYTHROID  ITQRQEIENQYRSLLDRAEERRRLLQRYNEFLLAYEAGDMLEWIQEKKA...ENTGVELDDVWELQKK

FDDFQKDLKANESRLKDINKVAEDLDSEGLMAEEVQAVQQQEVYGMMPRDETDSKTASPWKSARLMVHTVA
           |  | ||| | || ||||||| ||      |  | |
           FDEFQKDLNTNEPRLRDINKVADDLLFEGLLTPEGAQIRQ......

BalI                PfIMI
                 ⟶                 ⟶
           TFNSIKELNERWRSLQQLAEERSQLLGSAHEVQRFHRDADETKEWIEEKNQALNTDNYGHDLASVQALQRK    12
           ||| || ||||  |   |   ||||||| ||   | |    ||  |  ||  ||           ||||
           ......ELNARWGSLQRLADEQRQLLGSAHAVEVFHREADDTKEQIEKKCQALSAADPGSDLFSVQALQRR

HEGFERDLAALGDKVNSLGETAERLTQSHPESAED
           ||||||||  | ||| ||||||||    | | | |
           HEGFERDLVPLGDKVTILGETAERLSESHPDATED
```

FIG. 3a

| | Calmodulin Binding Protein | Proposed Active Sequence |
|---|---|---|
| 1 | Non-erythroid Spectrin | KTASPWKSARLMVHTVATFNSIKE |
| 2 | Smooth Muscle MLCK | MARRKWQKTGHAVRAIGRLSSS |
| 3 | Skeletal Muscle MLCK | LMKRRWKKNFIAVSAAANRFKK |
| 4 | Calcium⁺² Pump | LRRGQILWFRGLNRIQTQIKVVNAFSS |
| 5 | Calmodulin Kinase II | KLFNARRKLKGAILTTMLATRNFS |
| 6 | Mastoparan X | INWKGIAAMAKKLL |

5,182,262

CALMODULIN BINDING PEPTIDE DERIVATIVES OF NON-ERYTHROID ALPHA SPECTRIN

FIELD OF THE INVENTION

The present invention relates to calmodulin binding peptide derivatives of non-erythroid alpha spectrin, compositions thereof, and methods of using the peptide derivatives.

BACKGROUND OF THE INVENTION

Calcium is one of the "second messengers" that serves by relaying chemical and electrical signals within cells. A key component in this signal transduction involves the binding of calcium to a ubiquitous intracellular receptor protein called calmodulin. Calmodulin, in turn, interacts with a number of protein targets in a calcium dependent manner thereby altering a number of complex biochemical pathways that can affect the overall behavior of cells. A number of drugs with diverse applications are known to work by binding to calmodulin and thus alter the cell's response to changes in intracellular calcium. One of the most abundant and widely expressed calmodulin binding proteins is the alpha subunit of non-erythroid spectrin.

A number of calmodulin targeted drugs have been in use for some time. For instance, U.S. Pat. No. 2,645,640, discloses Chlorpromazine and related phenothiazine derivatives which are calmodulin binding drugs widely used as tranquilizers and sedatives. In addition, U.S. Pat. No. 4,117,118 discloses Cyclosporin A which is a cyclic polypeptide used as an immunosuppressive agent. This drug is thought to work by inhibiting calmodulin mediated responses in lymphoid cells. Toxic side effects from this drug have been noted, so other compounds with similar activity may allow alternative treatments with less toxicity.

One object of the present invention is to provide polypeptide sequences and compositions thereof derived from spectrin which binds calmodulin in a calcium dependent manner.

Another object of the invention is to provide clinical, pharmacological, and industrial uses of synthetic polypeptides whose structures are derived from spectrin and are capable of binding to calmodulin.

SUMMARY OF THE INVENTION

The present invention relates to a polypeptide and derivatives thereof deduced from the native structure of non-erythroid alpha spectrin and compositions thereof. The invention further relates to methods of using the polypeptide, such as methods for treating disorders including prophylaxis against organ and tissue transplant rejection or treatment of autoimmune disorders.

Accordingly, the present invention is based on an active sequence of amino acids found within the native structure of non-erythroid alpha spectrin that is capable of binding to calmodulin in a calcium dependent fashion. The general location of this active site was initially deduced through functional studies on genetically engineered (deletion mutant) spectrin molecules and the precise functional site was later confirmed through the analysis of a synthetic peptide, comprised of 24 amino acids, which was recognized from the putative function site of the natural protein. Thus, one embodiment of the invention is 24 amino acids in length and composed of the following linear sequence of residues: Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu.

Other considerations would suggest that shortened or substituted derivatives of this peptide are also functional. In particular, the 15-mer sequence contained within the above mentioned 24-mer, which begins with Pro-Trp-Lys . . . and ends with . . . Ala-Thr-Phe, is another embodiment of the invention considered to be functional since this segment is predicted to fold into an alpha-helical conformation and is considered as the minimal folding unit within the native protein capable of function. Therefore, any peptide derivative ranging in size from the 15-mer up to the 24-mer should be included in this patent application.

Other important features thought to be essential for activity include the unique distribution of charged and hydrophobic amino acids within the native sequence, therefore any conservative substitutions of charged or hydrophobic residues with other amino acid residues or other chemical moieties that would preserve the charge or hydrophobic character of that portion should be covered by this patent.

Furthermore, substitutions or additions at the termini of these peptides are not likely to abolish activity and therefore any peptide derivatives containing the above-mentioned sequences within their interior portions that are capable of mimicing the above mentioned native spectrin sequences in their ability to bind to calmodulin in a calcium dependent manner should also be covered by this application.

All studies to date demonstrating the biological activity of this peptide have involved testing of purified components in vitro. However, as discussed in detail hereinbelow, the in vitro test results readily correlate in vivo. Biological activity of the claimed synthetic polypeptide has been demonstrated by four independent calmodulin binding assays. The peptide binds to calmodulin-sepharose affinity columns and can be specifically eluted in the absence of calcium. The peptide competes for binding to calmodulin with a calmodulin stimulated cyclic-nucleotide phosphodiesterase, as well as with several other calmodulin binding proteins detected in brain. Furthermore, the binding is evident by peptide fluorescence changes that occur upon mixing the peptide with calmodulin in the presence of calcium. We have not defined the limits of a minimal size active peptide derived from the active site of spectrin and it is likely, based on the structures of several calmodulin binding peptides derived from other proteins, that shorter, longer, or substituted versions of the sequence will also show activity. For this reason the term "derivatives" should apply to any modified peptides whose structure is based on our active peptide and whose action is based on their ability to bind calmodulin.

BRIEF DESCRIPTION OF THE DRAWINGS

FIG. 2 shows a comparison of homologous sequences of non-erythroid (fodrin) and erythroid spectrins within the proposed calmodulin binding region of the fodrin alpha chain;

FIGS. 3A and 3B show a comparison of the proposed calmodulin binding sequence of alpha-fodrin with functional sites identified in other calmodulin binding proteins.

DETAILED DESCRIPTION OF THE INVENTION

Figure 1A:
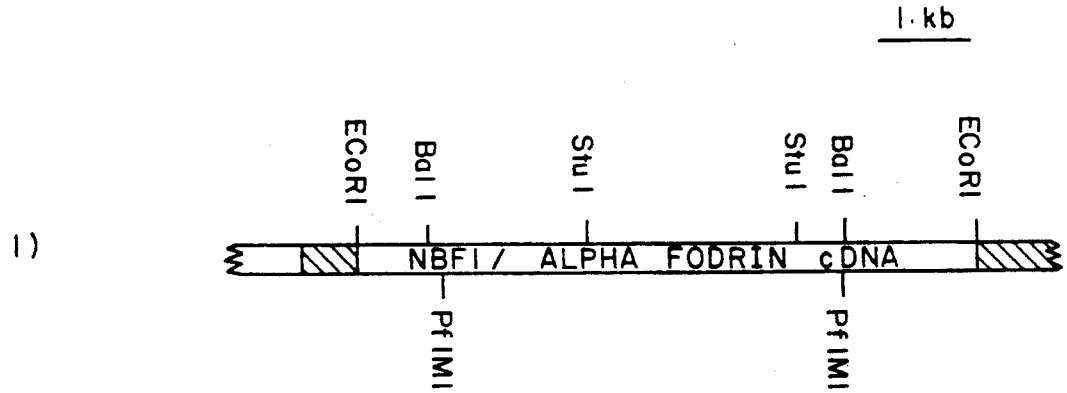
FIGS. 1A and 1B show the construction and functional analysis of recombinant alpha-fodrin fusion-proteins.

An important function of the mammalian non-erythroid alpha-spectrin chain (alpha-fodrin) that distinguishes it from the closely related erythroid isoform is its ability to bind calmodulin (Glenney, J. R., et al., Proc. Natl. Acad. Sci. U.S.A., Vol. 79, pp. 4002-4005 (1982)). By analysis of a series of deleted recombinant spectrin fusion-proteins we have identified a region in the non-erythroid alpha chain involved in calcium dependent binding of calmodulin. The region is distinctive in that the sequence is absent from the homologous domain of the erythroid alpha chain and diverges from the normal internal repeat structure observed throughout other spectrins. In order to determine limits of this functional site, a synthetic peptide as small as 24 residues, derived from a region between repeats 11 and 12, was shown to compete with either recombinant or brain alpha spectrin in binding to calmodulin. The active peptide was composed of the following sequence: Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu. A key to the above-mentioned peptide abbreviations is shown below:

| Peptide | Abbreviation | Peptide | Abbreviation |
|---|---|---|---|
| Lysine | Lys | Methionine | Met |
| Threonine | Thr | Valine | Val |
| Alanine | Ala | Phenylalanine | Phe |
| Proline | Pro | Asparagine | Asn |
| Serine | Ser | Isoleucine | Ile |
| Arginine | Arg | Glutamic Acid | Glu |
| Leucine | Leu | | |

Comparison of this sequence with other diverse calcium dependent calmodulin binding proteins has revealed a structural motif common to all of these proteins, namely, clusters of hydrophobic residues interspersed by basic residues. When folded into an alpha helical conformation these binding sites are predicted to form amphipathic structures.

A general feature that characterizes all spectrin family members is their highly repetitive structure. The spectrin repeat was first described, based the on sequence from the erythroid alpha and beta chains, as a 106 amino acid repetitive motif with internal homology of 15-35% (Speicher, D. W., et al., Nature, Vol. 311, pp. 177-180 (1984)). Typical spectrin repeat sequences comprise most of the erythroid spectrin sequence and predict three helical segments interspersed by turn regions; these repetitive folded units can account for the extended rod-like structure of erythrocyte spectrin. (Speicher, D. W., et al., Nature, Vol. 311, pp. 177-180). Spectrin-like repeats are now recognized in all spectrins (Leto, T. L., et al., Mol. Cell. Biol., Vol. 8, pp. 1-9 (1988), McMahon, A. P., et al., Differentiation, Vol. 34, pp. 68-78 (1987), Birkenmeier, C. S., et al., Proc. Natl. Acad. Sci. U.S.A., Vol. 82, pp. 5671-5675 (1985), Wasernius, V. M., et al., EMBO J., Vol. 4, pp. 1425-1430 (1985), Baron M. D., et al., J. Biol. Chem., Vol. 262, pp. 17,623-17,629 (1987), Davison, M. D., et al., Cell, Vol. 52, pp. 159-160 (1988), Curtis, P. J., et al., Gene, Vol. 36, pp. 357-362 (1985), and Winkelmann, J. C., et al., Blood, Vol. 72, pp. 328-334 (1988)) and have enabled identification of some of the more divergent members of this family of cytoskeletal proteins including alpha-actinin (Baron M. D., et al., J. Biol. Chem., Vol. 262, pp. 17,623-17,629 (1987)) and the Duchenne's muscular distrophy protein, dystrophin (Davison, M. D., et al., Cell, Vol. 52, pp. 159-160 (1988)).

In our efforts to define structure-function relationships in non-erythroid alpha-spectrin (alpha-fodrin) we have analyzed the amino acid sequences deduced from cDNA clones. Like erythroid alpha-spectrin, most of the non-erythroid alpha-spectrin is composed of regular 106 amino acid repeats, though two regions diverge from this pattern. These are likely sites for specialized function. The first lies within the carboxyl-terminal domain (Leto, T. L., et al., Mol. Cell. Biol., Vol. 8, pp. 1-9 (1988)), where actin filaments interact, while the other, located between repeats 11 and 12, is a region which we show here to be the site of interaction with calmodulin. This region was previously noted for its divergence from the normal repeat-like structure; while earlier portions of repeats 11 and 12 contain sequence characteristic of other repeats, the eleventh repeat is unusual in that it is 142 amino acids in length (McMahon, A. P., et al., Differentiation, Vol. 34, pp. 68-78 (1987)).

Calmodulin binding is the most remarkable property that functionally distinguishes the non-erythroid alpha chain from the closely related erythroid isoform (Glenney, J. R., et al., Proc. Natl. Acad. Sci., Vol. 79, pp. 4002-4005 (1982)). Consistent with this observation the erythroid and non-erythroid alpha chains exhibit their greatest divergence in primary structure within this calmodulin binding region.

Materials and Methods

Construction of Expression Vectors—Recombinant spectrin fusion-proteins were expressed in Escherichia coli strain JM109 using the beta-galactosidase expression vector pBluescript (Stragene, San Diego, Calif.). A human neuroblastoma alpha-spectrin (alpha-fodrin) cDNA (NBF-1 (Leto, T. L., et al., Mol. Cell Biol., Vol. 8, pp. 1-9 (1988)) was subcloned into the Eco RI site of this plasmid. The protein sequence decoded from the 5' end of this clone was identical to the sequence deduced from a human fibroblast alpha-spectrin cDNA (starting at position 1192 of clone #3 (McMahon, A. P., et al., Diffentiation, Vol. 34, pp. 68-78 (1987)). This construction (designated pBS-NBF1) enabled expression of a protein composed of the carboxyl-terminal half of the a subunit (repeats 11-21) which was fused with 35 amino terminal residues of beta-galactosidase (FIG. 1A). Several modified fusion-proteins were designed from this clone using restriction sites which created various in frame deletions while preserving the same carboxyl-terminal domain of alpha-fodrin (repeats 20-21) in all cases (FIG. 1A). Each of these deleted constructs was confirmed by DNA sequencing using synthetic 17 base oligonucleotide primers which hybridized at sites close to the restriction cleavage sites.

Characterization of Récombinant Proteins

Transformants expressing the recombinant proteins were screened with antibody or calmodulin probes, either directly after growth of colonies on nitrocellulose filters, or by probing nitrocellulose electroblots of bacterial lysate proteins which were separated on SDS-PAGE gels.

Colony screening involved growing cells on nitrocellulose filters placed over agar media lacking isopropyl-beta-D-thiogalactopyranoside (Sigma, St. Louis, Mo.) (IPTG) and then transferring these filters to plates containing IPTG when the colonies had reached a size of 1-2 mm in diameter. Following an additional 2-3 hours incubation at 37° C. the colonies were lysed by exposing the filters to a chloroform saturated vapor (Young, R. A., et al., *Proc. Natl. Acad. Sci.*, Vol. 80, pp. 1194-1198 (1983)). These filters were then probed by the methods described below. Expression of the recombinant fusion-proteins in liquid cultures was induced by addition of 5 mM IPTG to cultures which had reached an absorbance of 0.5 at 600 nm, followed by an additional 2-3 hours of growth at 37° C. Cells pellets from these cultures were harvested and lysed at 95° C. for 3 minutes in 1.0% SDS, 1 mM EDTA, 50 mM Tris HCl, pH 6.9. This material was electrophoresed in SDS-polyacrylamide gels (10%) and electroblotted by standard procedures (Towbin, H., et al., *Proc. Natl. Acad. Sci.* Vol. 76, pp. 4350-4354 (1979)). These blots were probed with antibodies reactive against brain spectrin (a generous gift of Dr. Alan Harris, Yale University), which were in turn detected with [$^{125}$I] labeled staphylococcus protein A as described by Harris, A. S., et al., *Biochim. Biophys. Acta*, Vol. 830 p, pp. 147-158 (1985). Calmodulin binding proteins were identified by probing the nitrocellulose blots With biotinylated calmodulin (a generous gift form Dr. Randall L. Kincaid, National Institutes of Health), which was detected by streptavidin-alkaline phosphatase conjugates. Methods for the preparation and use of the biotinylated calmodulin probe have been described in detail elsewhere (Billingsley, M. L., *Proc. Natl. Acad. Sci.*, Vol. 82, pp. 7585-7589 (1985)).

DNA Sequence Analysis—All DNA sequences were determined by standard dideoxynucleotide chain termination methods using either sequenase (United States Biochemical, Cleveland, Ohio) or the large fragment of DNA polymerase I (Sanger, F., et al. *Proc. Natl. Acad. Sci.*, Vol. 74, pp 5463-5467 (1977)). The alpha-fodrin sequencing templates were derived from the same plasmid clones used for expression studies. Prior to sequencing the plasmid DNA was denatured in 0.2M NaOH and 1 mM EDTA, precipitated with ethanol, and annealed to sequencing primers as previously described (Chen, E. Y., et al. *DNA*, Vol 4, pp. 165-170 (1985)). The erythroid alpha-chain protein sequence was deduced from two human fetal liver cDNA's (alpha-3 & alpha-5) which were initially cloned from an expression library using antibody probes (Winkelmann, Jr., et al., *Blood*, Vol. 72, pp. 328-334 (1988)). Their deduced protein sequences were aligned with previously published peptide sequence (Speicher, D. W., et al., *Nature*, Vol. 311, pp. 177-180 (1984)).

Peptide Synthesis and Purification—The synthetic calmodulin binding peptide designed from alpha-fodrin sequence (sequence given in FIG. 3) was prepared by standard solid-phase synthetic methods using an Applied Biosystems 430A automated synthesizer. The product was cleaved from the resin with hydrofluoric acid and affinity purified by chromatography on calmodulin-agarose (Pharmacia). The peptide was bound to calmodulin-agarose in the presence of 6M urea, 100 mM KCl, 100 mM TrisCl, 2 mM CaCl$_2$, pH 7.6 and subsequently eluted with the same buffer containing 5 mM EGTA in place of CaCl$_2$. The affinity purified material, when analyzed by reverse phase HPLC on a C$_4$ column, eluted as one prominent peak. Estimates of the peptide concentration were calculated form an assumed extinction coefficient of 5500 cm$^{-1}$ M$^{-1}$ based on the single tryptophan residue present in this peptide.

Results and Discussion

Figure 1B:
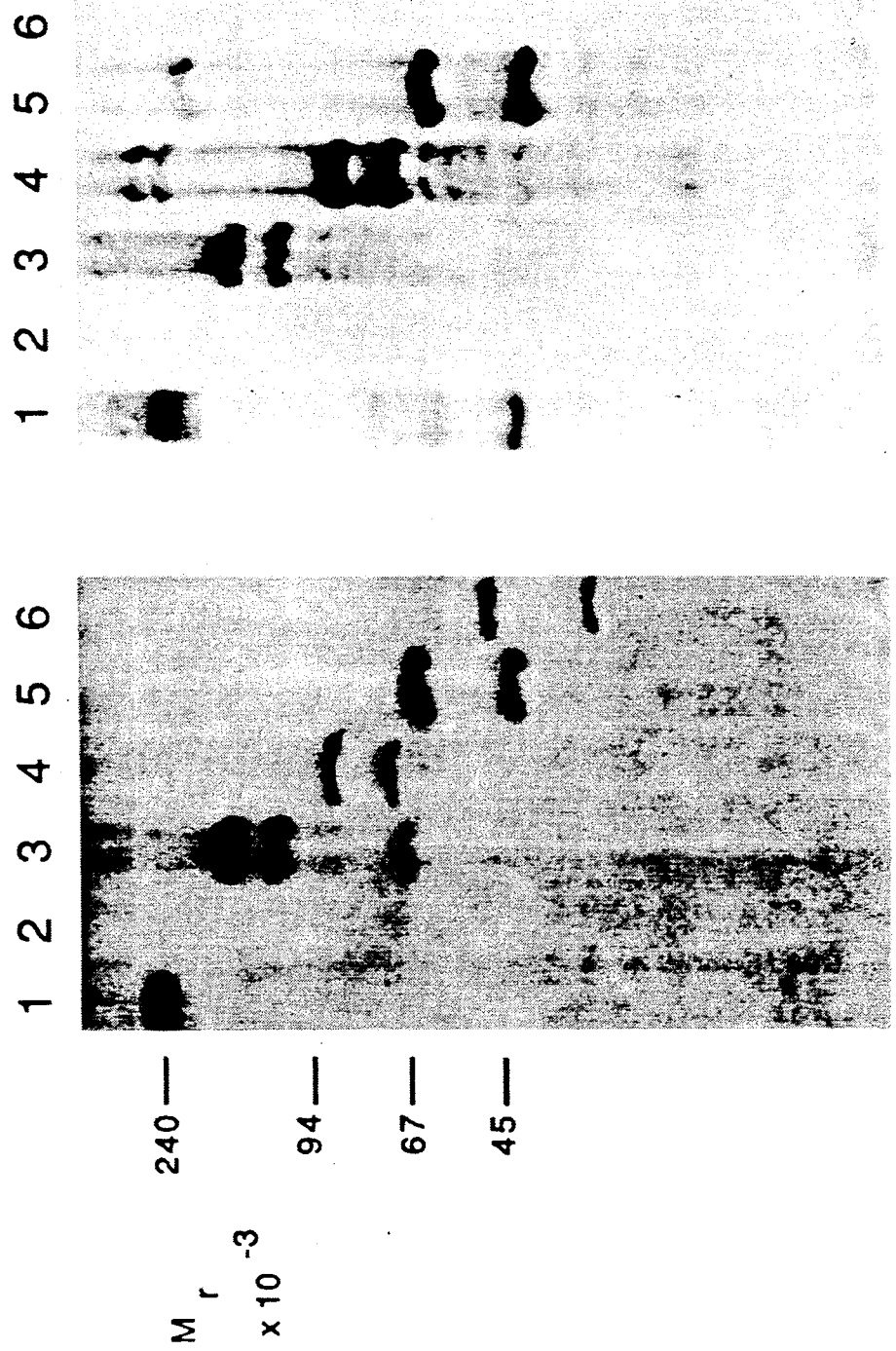

The bluescript plasmid was an efficient expression system for production of stable and functional recombinant spectrin in *E. Coli*. The non-erythroid alpha-spectrin clone (pBS-NBF1) was obtained by directly subcloning the Eco RI fragment of a human neuroblastoma cDNA (NBF1) (Leto, T. L., et al., *Mol. Cell Biol.*, Vol. 8, pp. 1-9) into the same unique restriction site of this plasmid. The resulting construct, which joined sequence encoding the carboxyl terminal half of alpha-fodrin in frame with sequence encoding the 35 amino terminal residues of the beta-galactosidase, gave rise to a fusion-protein capable of binding to calmodulin (FIG. 1B). Transformants expressing recombinant spectrin could be distinguished from others based on their apparent slower rate of growth, suggesting that this foreign protein had adverse effects on the host cells. Large amounts of fusion protein could be detected in the lysates of cells grown in cultures induced with IPTG (isopropyl-beta-D-thiogalactopyranoside). Analysis of the induced proteins, following separation in SDS-PAGE gels and electroblotting onto nitrocellulose, showed two prominent immunoreactive bands, the larger of size consistent with the carboxyl terminal half of the alpha chain, while the other was thought to be a major breakdown product (FIG. 1B, lane 3). The same inducible proteins were detected on nitrocellulose blots probed with biotin labeled calmodulin and streptavidinalkaline phosphatase reagents. Binding of calmodulin to these recombinant proteins was calcium dependent, a known property of intact alpha-fodrin Glenney, J. R., et al., *Proc. Natl. Acad. Sci.*, Vol. 79, pp. 4002-4005 (1982)), since inclusion of 1 mM EGTA in the probe solution abolished binding (data not shown). A control homogenate from bovine brain probed in the same way showed the same series of calmodulin binding proteins previously recognized by this calmodulin probe (Kincaid, R. L., et al., *Proc. Natl. Acad. Sci.* Vol. 84, pp. 1118-1122 (1987)), among them the alpha chain of brain spectrin was the principle calmodulin binding protein detectable by this blotting method (FIG. 1B, lane 1). A lysate derived from an *E. coli* transformant which lacked the spectrin cDNA insert did not express any proteins with reactivity with either antibody or calmodulin reagents (FIG. 1B, lane 2).

Efforts to localize the region of the non-erythroid spectrin alpha-chain critical to calmodulin binding involved the analysis of a series of recombinant proteins which were deleted to varying degrees, using restriction enzymes that created in frame deletions of the spectrin cDNA coding sequence (FIG. 1A). Confirmation of the proper deletions by DNA sequencing was necessary since some enzymes cleaved the cDNA at more than two sites. Probing the deleted fusion-proteins on nitrocellulose electroblots with the antibody and calmodulin reagents revealed a series of shortened immunoreactive proteins of predicted size, as well as one major breakdown product, which was consistent with the presence of the same proteolytically susceptible site in all of these recombinant proteins (FIG. 1B, lanes 4-6). Only one of the deleted cDNA's, which was cleaved with Bal I and lacked sequence encoding unusual non-repeat-like structure at the end of repeat 11, produced an anti-fodrin reactive fusion-protein which was unable to bind calmodulin (FIG. 2B, lane 6). This region of repeat 11 was previously noted for its divergence from the normal repeat-like structure; while earlier portions of repeats 11 and 12 contain sequence characteristic of other repeats, the eleventh repeat is unusual in that it is 142 amino acids in length (McMahon, A. P., et al., *Differentiation*, Vol. 34, pp. 68-78 (1987)). Thus, like several specialized functional sites identified in other spectrin chains, including the phosphorylation site of the erythroid beta chain (Winkelmann, J. C., et al., *Blood*, Vol. 72, pp. 328-334 (1988)) and actin binding regions of the non-erythroid alpha chain (Leto, T. L., et al., *Mol. Cell. Biol.*, Vol. 8, pp. 1-9 (1988)) and alpha-actinin (Baron M. D., et al., *J. Biol. Chem.*, Vol. 262, pp. 17,623-17,629 (1987)), the region of alpha fodrin thought to function in calmodulin binding also diverges from normal spectrin repeat-like structure.

The construction and functional analysis of recombinant alpha-fodrin fusion-proteins is shown in FIG. 1.

FIG. 1(a)(1) shows the construction of an alpha-fodrin cDNA fragment (pBS-NBF1) for expression in *E. Coli*. The Eco RI fragment of a neuroblastoma alpha-fodrin cDNA, NBF1 (Leto, T. L., et al, *Mol. Cell. Biol.*, Vol. 8, pp. 1-9 (1988)), was subcloned into the same site within the lac Z gene (▩) of the Bluescript KS⁻ plasmid (Stratagene, San Diego, Calif.), thereby fusing fodrin sequence to 35 amino-terminal residues of the vector encoded beta-galactosidase. In frame deletions of internal fodrin sequence were made from the indicated restriction sites.

FIG. 1(a)(2) shows the alignment of homologous spectrin repeats (106 amino acids) encoded by the alpha-fodrin cDNA clone NBF1 Eco RI fragment.

FIG. 1(a)(3) shows a schematic representation of the locations of sequence deletions made from restriction sites within the fodrin cDNA, with spliced sequences indicated below each cleavage site. All splice sites were confirmed by sequencing the deleted clones with primers that annealed near these sites. While all deleted proteins contain the C-terminal domain (repeats 20-21), only the Bal I cleavage removes sequence encoding the non-repeat-like sequence (■) between repeats 11 and 12.

FIG. (1)(b) shows the of recombinant proteins expressed by transformants described in FIG. 1(a) with antibody against brain spectrin (Harris, A. S., et al, *Biochim. Biophys. Acta.*, Vol. 830, pp. 147-158 (1985)) (left) or biotinylated calmodulin (right). Transformed cells were grown in 3 ml cultures and induced with 5 mM isopropylthio-galactopyranoside as described in Huynh, T. V., et al, *Molecular Cloning* (ed Glover, D. M.), pp. 49-78 (IRL Press, Oxford, 1985). Cell lysates derived from 1 ml of culture medium were separated on 10% polyacrylamide-SDS gels and blotted onto nitrocellulose by standard protocols (Harris, A. S., et al, *Biochim. Biophys. Acta.*, Vol. 830, pp. 147-158 (1985)). Anti-fodrin was detected with [$^{125}$I]-*Staphlococcus aureus* protein A as described in Harris, A. S., et al, *Biochim. Biophys. Acta.*, Vol. 830, pp. 147-158 (1985). Use of biotinylated calmodulin and detection with streptavidin-phosphatase reagents has been described elsewhere (Billingsley, M. L., et al, *Proc. Natl. Acad. Acad.* U.S.A., Vol. 82, pp. 7585-7589 (1985)). Column 1 in FIG. 1(b) shows the results when using 100 ug of a total bovine brain homogenate; column 2 shows the results of a lysate from a Bluescript transformant lacking inserted cDNA; columns 3-6 show the results of lysates from transformants expressing the undeleted (3), Stu I deleted (4), Pf1MI deleted (5) and Bal I deleted (6) fodrin cDNAs, respectively. The Bal I deleted clone is the only one that expresses an immunoreactive protein which is not detected with the calmodulin probe.

In light of this data the structure of the homologous domain of the erythroid alpha chain was of interest, since this isoform does not bind calmodulin. The erythroid sequence was determined from two independent fetal liver cDNA clones (Winkelmann, J. C., et al, *Blood*, Vol. 72, pp. 328-334 (1988)), designated alpha-3 & alpha-5. These two cDNA clones contained identical nucleotide sequences in the overlapping region analyzed and their deduced protein sequences aligned precisely with previously reported peptide sequence which was assigned to the beginning of repeat 11 (Speicher, D. W., et al., *Nature*, Vol. 311, pp. 177-180 (1984)). Comparison of the sequences of the erythroid and non-erythroid proteins in this putative functional domain has revealed the structural basis for their functional difference (FIG. 2). The non-erythroid alpha-spectrin sequence, when aligned with the homologous erythroid sequence, deduced from two independent cDNA clones, appeared to be the most structurally divergent region recognized between the erythroid and non-erythroid isoforms (FIG. 2).

FIG. 2 shows a comparison of homologous sequences of non-erythroid (fodrin) and erythroid spectrins within the proposed calmodulin binding region of the fodrin alpha chain. The sequences begin with position 1 of spectrin repeat 11 defined by Speicher and Marchesi (Speicher, D. W., et al, *Nature*, Vol. 311, pp. 177-180 (1984)). The fodrin sequence deduced from NBF1 is identical to deduced sequence previously reported by McMahon et al (starting at position 1128 of clone 3 (McMahon, A. P., et al, *Differentiation*, Vol. 34, pp. 68-78 (1987)). The erythroid sequence was determined from two independent fetal liver cDNA clones (designated alpha-3 and alpha-5), which were selected by antibody screening procedures (Winkelmann, J. C., et al, *Blood*, Vol. 72, pp. 328-334 (1988)) and shown to match precisely with previously reported repeat 11 peptide sequence (Speicher, D. W., et al, *Nature*, Vol. 311, pp. 177-180 (1984)). Arrows indicate the starting point of fodrin sequence that is deleted by the restriction enzymes indicated above. Sequence homologous to the proposed calmodulin binding site of alpha-fodrin (underlined) is absent from the erythroid chain, yet the adjacent regions exhibit higher homology between isoforms than most other regions previously compared (Leto, T. L., et al, *Mol Cell. Biol.*, Vol. 8, pp. 1-9 (1988) and McMahon, A. P., et al, *Differentiation*, Vol. 34, pp. 68-78 (1987)).

Accordingly, while the two alpha chains show a rather striking homology in the earlier portions of both repeats 11 and 12, a gap of 37 residues in the erythroid sequence was required for optimum alignment of the highly homologous regions. In contrast to the non-erythroid sequence, the erythroid eleventh repeat is similar in length to other normal spectrin repeats. All other available sequence previously compared between human erythroid and non-erythroid alpha chains, obtained from repeats 7-9, 14-16 and 19, showed the two isoforms to be otherwise uniformly homologous, with about 55% identical amino acid sequences (Leto, T. L., et al, *Mol. Cell. Biol.*, Vol. 8, pp. 1-9 (1988) and McMahon, A. P., et al, *Differentiation*, Vol. 34 pp. 68-78 (1987))

Comparison of limited sequences between mouse and human erythroid cDNAs suggested that the mammalian erythroid alpha spectrin chain is a rapidly diverging derivative of the highly conserved non-erythroid alpha isoform (Leto, T. L., et al, *Mol. Cell. Biol.*, Vol. 8, pp. 1-9 (1988), McMahon, A. P., et al, *Differentiation*, Vol. 34, pp. 68-78 (1987), and Curtis, P. J., et al, *Gene*, Vol. 36, pp. 357-362 (1985)). Unlike mammalian erythrocytes, which express a unique alpha spectrin isoform, avian erythrocytes express the same non-erythroid alpha chain, which is capable of calmodulin binding (Glenney, J. R., et al, *Proc. Natl. Acad. Sci. U.S.A.*, Vol. 79, pp. 4002-4005 (1982)). Calmodulin binding seems to be an important evolutionarily conserved function, since it has been observed with a Drosophila spectrin as well (Dubreuil, R., et al, *J. Cell Biol.*, Vol. 105, pp. 2095-2102 (1987)). Thus, it is likely that the gene for the recently diverged and specialized mammalian erythroid alpha chain evolved by gene duplication and subsequent deletion of this functional region from a precursor related to the non-erythroid alpha spectrin gene.

Accurate predictions of the calmodulin binding sequence within alpha-fodrin relied on comparisons with sequences in a number of well characterized calcium dependent calmodulin binding proteins (Lukas, T. J., et al, *Biochemistry*, Vol. 25, pp. 1458-1464 (1986), Blumenthal, D. K., et al, *Proc. Nat. Acad. Sci. U.S.A.*, Vol. 82, pp. 3187-3191 (1985)), James, P., et al, *J. Biol. Chem.*, Vol. 263, pp. 2905-2910 (1988), Hanley, R. M., et al, *Science*, Vol. 237, pp. 293-297 (1987), and Malencik, D. A., et al, *Biochemistry*, Vol. 23, pp. 2420-2428 (1985)). A list of several recently identified calmodulin binding sequences is given in FIG. 3, along with a proposed functional sequence derived from the end of the eleventh repeat of alpha-fodrin ( . . . KTASPWKSARLMVHTVATFNSIKE . . . ) which has structural features compatible with those observed in the other proteins. The following chart shows the symbols for the amino acid code.

| Amino Acid | Abbreviation | Amino Acid | Abbreviation |
|---|---|---|---|
| Alanine | A | Leucine | L |
| Arginine | R | Lysine | K |
| Asparagine | N | Methionine | M |
| Aspartate | D | Phenylalanine | F |
| Cysteine | C | Proline | P |
| Glutamate | E | Serine | S |
| Glutamine | Q | Threonine | T |
| Glycine | G | Tryptophan | W |
| Histidine | H | Tyrosine | Y |
| Isoleucine | I | Valine | V |

FIG. 3 shows a comparison of the calmodulin binding sequence of alpha-fodrin with functional sites identified in other calmodulin binding proteins.

FIG. 3(a) shows that all functional sequences are comprised of hydrophobic stretches interspersed with basic residues. The sequences are aligned relative to tryptophan residues commonly observed at the beginning of these active sites.

Figure 3B:
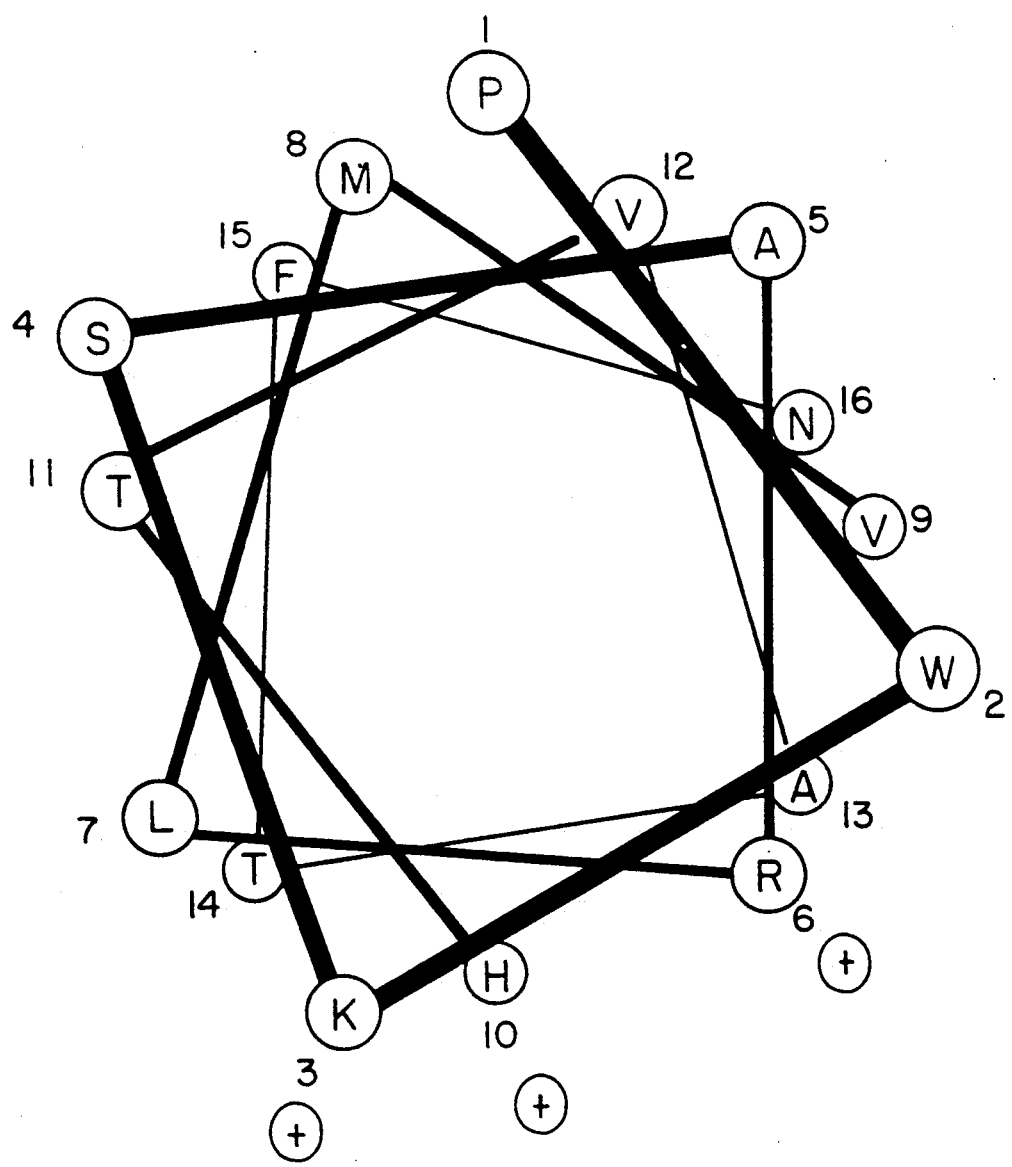

FIG. 3(b) shows an alpha-helical representation of the proposed functional site of alpha-fodrin which reveals a structural motif common to all of these active sequences. The fodrin sequence beginning with PKW . . . and ending with . . . TFN has a high probability for forming an alpha-helix according to predictions based on the criteria described by Chou and Fasman (Chou, P. Y., et al, *Biochemistry*, Vol. 13, pp. 211-222 (1974)). In this conformation basic and non-polar residues segregate onto opposite faces of the helix. Sequences 2-6, as well as other model peptides (Cox. J. A., et al, *J. Biol. Chem.*, Vol. 260, pp. 2527-2534 (1984)), assume higher alpha-helical contents upon binding alpha-helical contents upon binding to calmodulin and exhibit the same amphipathic structure in this conformation.

While comparisons at the primary sequence level does not suggest a common binding site, detailed physical studies using both native and model synthetic peptides have allowed identification of consensus features considered essential to calmodulin binding. Most of these active sequences are either predicted or observed to fold into alpha-helical conformations when bound to calmodulin (Lukas, T. J., et al, *Biochemistry*, Vol. 25, pp. 1458-1464 (1986), Blumenthal, D. K., et al, *Proc. Nat. Acad. Sci. U.S.A.*, Vol. 82, pp. 3187-3191 (1985)), James, P., et al, *J. Biol. Chem.*, Vol. 263, pp. 2905-2910 (1988), Hanley, R. M., et al, *Science*, Vol. 237, pp. 293-297 (1987), Malencik, D. A., et al, *Biochemistry*, Vol. 23, pp. 2420-2428 (1985), Cox. J. A., et al, *J. Biol. Chem.*, Vol. 260, pp. 2527-2534 (1984), O'Neil, K. T., et al, *Science*, Vol. 236, pp. 1454-1456 (1987), Klevit, R. E., et al, *Biochemistry*, Vol. 24, pp. 8152-8157 (1985), and Seeholzer, S. H., et al, *Proc. Nat. Acad. Sci. U.S.A.*, Vol. 83, pp. 3634-3638 (1986)). Some of the peptides demonstrating high affinity binding are surprisingly small, as short as 15 Å in length (Cox. J. A., et al, *J. Biol. Chem.*, Vol. 260, pp. 2527-2534 (1984)). Furthermore these sequences generally contain a number of hydrophobic residues that are interspersed by basic residues, such that when folded into helical conformations the charged and hydrophobic amino acids segregate onto opposite sides of the helix.

Calculations of the hydrophobic moment, which is an index of the amphiphilcity of these helical segments, indicate calmodulin binding peptides are "surface seeking" structures (Erickson-Viitanen, S., et al, *Meth. in Enzymol.*, Vol. 139, pp. 455-478 (1987)). Overall charge also appears to contribute to binding since all active sequences contain at least three basic residues and no intervening acidic amino acids, although the position of these charges along the length of the helix can vary. The proposed functional sequence of alpha-fodrin, in addition to being absent from the homologous domain of erythroid spectrin, conforms well to the above mentioned structural properties defined for this class of calmodulin binding proteins. Projection of this sequence into a helical wheel illustrates its amphipathic character (FIG. 3B). It is interesting to note that the proposed binding sequence of fodrin contains serine and proline near the beginning, which are residues that show strong preference for alpha-helix N-terminal cap and initiator positions (Richardson, J. S., et al., *Science*, Vol. 240, pp. 1648-1652 (1988)).

The calculated hydrophobic moment and mean hydrophobicity of the fodrin helical segment beginning with PWK . . . and ending with . . . ATF, are 0.4 and 0.19 kcal/mol respectively, which are close to values calculated for a number of other calmodulin binding sequences (Erickson-Viitanen, S., et al, *Meth. in Enzymol.*, Vol. 139, pp. 455-478 (1987)). Furthermore, this segment is predicted to be in an alpha-helical conformation according to Chou and Fasman criteria. (Chou, P. Y., et al, *Biochemistry*, Vol. 13, pp. 211-222, (1974)).

Moreover, the fodrin sequence contains other common features including a tryptophan, which shows preference for the beginning, and serine, which is a favored residue at the end of several of the active sequences. While it is clear that several of these calcium dependent calmodulin binding proteins have evolved independently, their similarity at the secondary structural level suggests that they interact with a common site on calmodulin.

In order to establish firmly the identity of the active site of fodrin a synthetic polypeptide was prepared based on the sequence proposed in FIG. 3 and tested for its ability to compete for binding to calmodulin. Like intact alpha-fodrin, the peptide appears to bind calmodulin in a calcium dependent manner. This property has enabled an affinity purification of the peptide on calmodulin-sepharose. The ability of this affinity purified material to compete directly with other calmodulin binding proteins was demonstrated by incubation of this peptide in the presence of the biotinylated calmodulin used to probe calmodulin binding proteins immobilized on nitrocellulose electroblots (FIG. 4).

Figure 4:
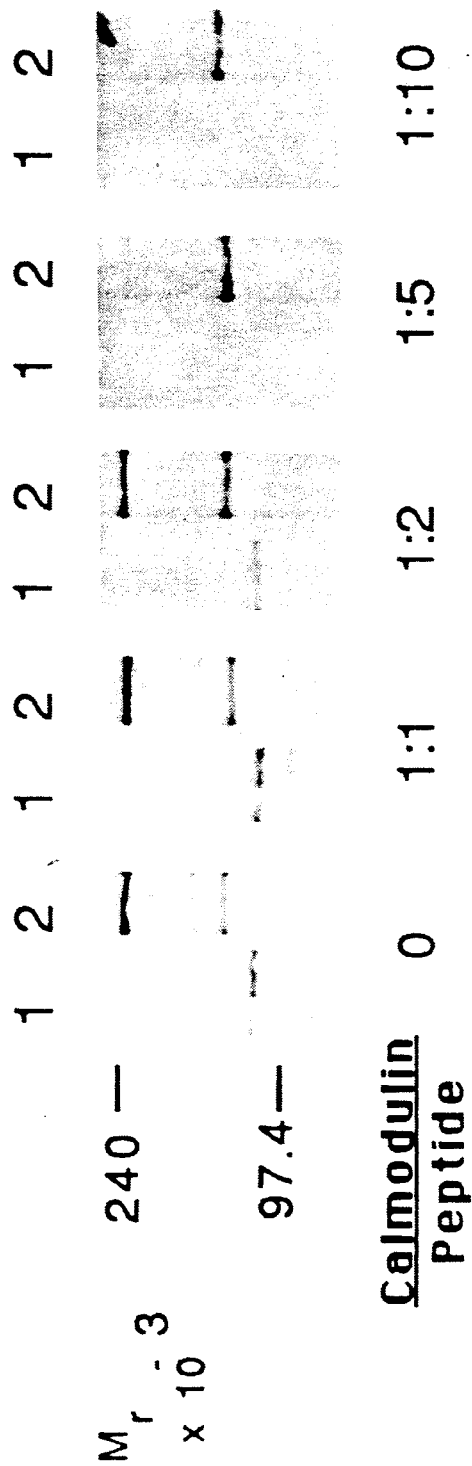
FIG. 4 shows the inhibition of calmodulin binding to intact and recombinant fodrin by a synthetic peptide corresponding to the proposed functional site of alpha fodrin.

FIG. 4 shows the inhibition of calmodulin binding to intact and recombinant fodrin by a synthetic peptide corresponding to the proposed functional site of alpha-fodrin. Nitrocellulose blots were prepared and probed as in FIG. 1b. using 1 ug/ml of biotinylated calmodulin and the molar ratios of calmodulin to synthetic peptide indicated below the lanes. Lane 1 shows results of a lysate which contains recombinant spectrin from 100 ul of induced E. coli cells from an undeleted NBF1-bluescript transformant; lane 2 shows results from 10 ug of crude brain bovine lysate, prepared as described in FIG. 1. Before use, the synthetic peptide defined in FIG. 3a was affinity purified by chromatography on calmodulin-agarose (Pharmacia). The peptide was bound to this matrix in the presence of 4M urea, 100 mM KCl, 20 mM TrisCl, 2 mM CaCl$_2$, pH 7.6 and subsequently eluted with the same buffer containing 5 mM EGTA in place of CaCl$_2$. The affinity purified peptide was shown to contain only one prominent peak and therefore homogeneous when analyzed by reverse phase HPLC on a C4 column. This peptide was first mixed with biotinylated calmodulin at the appropriate concentration as indicated in FIG. 4 and the mixture was then used to probe the nitrocellulose blots for one hour at room temperature. Estimates of the peptide concentration were based on an assumed extinction coefficient of 5500 cm$^{-1}$M$^{-1}$ due to the single tryptophan residue present in this sequence.

The potent inhibition of calmodulin binding to intact (240 KDa) and recombinant brain alpha-fodrin suggested that this short peptide has complete native activity, while, in contrast, competition for binding with another calmodulin binding protein (M$_r$~150 KDa) detected in the crude brain homogenate was not as apparent in FIG. 4, lane 2. Based on the concentrations of peptide and calmodulin used in this experiment, the affinity of this 24 residue peptide for calmodulin was estimated with a K$_D$<10$^{-7}$.

The calmodulin binding site of alpha-fodrin, unlike the other calmodulin binding proteins, is not a terminal sequence. Ferritin-calmodulin conjugates labelled fodrin close to the "head" region of fodrin dimers, when viewed by rotary-shadow electron microscopy (Tsukita, S., et al., J. Cell Biol., Vol. 97, pp. 574-578 (1983)), though it is difficult to relate this information directly to our primary sequence data. Our localization to the middle region of the alpha chain is consistent with that determined by Glenney et al. (Glenney, J. R., et al., J. Mol. Biol., Vol. 167, pp. 275-293 (1983)), who used proteolytic digests and monoclonal antibodies as markers.

Alpha-fodrin is one of the most abundant calmodulin binding proteins detectable in many tissues (Palfrey, H. C., et al., Proc. Nat. Acad. Sci., U.S.A. Vol. 79, pp. 3780-3784 (1982)), although to date no clear function has been ascribed to this interaction. This binding could modulate cytoskeleton-membrane interactions or serve as a significant reservoir of calcium and calmodulin on the membrane surface. Studies on expression of genetically altered fodrin chains may enable a critical assessment of the role of this interaction in eukaryotic cells.

The polypeptides of the present invention may be formulated as a composition when combined with conventionally known pharmaceutically acceptable carriers. For instance, the polypeptides of the present invention can be made into pharmaceutical compositions by combinations with appropriate medical carriers of diluents. The polypeptides can be dissolved in aqueous solution or in other suitable solvents such as ethanol for oral administration. The polypeptides can be made into tablet form, mixed in combination with starch, sugar or other inert carriers used to make tablets for oral administration. These polypeptides can also be prepared in aqueous solution, or in other solvents such as oils, propylene glycol or other common solvents used to make injectable solutions. These preparations can be administered as immunesuppressive or antipsychotic agents.

The following methods are exemplary and in no way limit the use of the invention.

The polypepetides of the present invention may be given as a pharmaceutical dosage either alone, or in the form of suitable salts, or in combination with other pharmaceutically active compounds.

The polypeptides in the case of injectable preparations may be formulated by dissolving or suspending them in aqueous solvents such as normal saline or 5% dextrose at concentrations ranging from 1-2000 milligrams per ml, preferably 10 mg/ml. The polypeptides may also be encapsulated into liposomal vesicles to assist in the passage of these compounds through cell membranes and enhance uptake by living cells. Such carrier preparations have been described in the case of encapsulation of the antibiotic, amphotericin B, into lipid vesicle (Lopez-Berenstein, G. Antimicrob. Agents Chemother., Vol. 31, pp. 675-678 (1987)). The dosage in this case would be identical to the injectable preparations described above.

The polypeptides, in the case of oral administration, could be prepared in tablet, capsule, granule, or powder form with suitable inert pharmaceutical carriers such as starch or cellulose or with diluents, buffering agents, preservatives or flavoring agents. The polypeptides can also be provided in solution form (e.g., aqueous or alcoholic) or dissolved or suspended in vegetable oils at concentrations ranging from 1 to 2000 mg/ml in the presence of other agents such as flavoring agents or preservatives. These preparations could be diluted further with milk or orange juice when administered orally.

The dose delivered varies with subject, dosage form, and method or period of administration, however in order to achieve desired affects it is recommended that the compounds be administered at 0.1-50 mg/kg, preferably 0.5-10 mg/kg, body weight-per day. The polypeptides should be given at a composition ranging from 0.1-100% by weight.

The following example further illustrates the composition of the present invention and will enable others skilled in the art to understand the invention more completely. It is understood that the invention is not limited to the Example below.

EXAMPLE 1

2 mg of the polypeptide of claim 1 as the active ingredient is combined with 187 mgrams of microcrystalline cellulose as a carrier, 9 mg of stearic acid and 2 mg of colloidal silica. These materials are pressed to form a tablet.

Methods of treating various diseases or disorders with the polypeptide or composition of the invention will hereinafter be described in greater detail.

EXAMPLE 2

A tablet is first formulated and prepared as in Example 1. The tablet is orally administered to a patient and represents a typical daily dosage.

EXAMPLE 3

Chemical Synthesis and Purification

The peptide inventions described herein are prepared by standard solid-phase peptide synthetic methods known in pharmaceutical practice (Linder W. & Robey "Automated Synthesis and Use of N-chloracetyl-modified Peptides for the Preparation of Synthetic Peptide Polymers and Peptide-protein Immunogens", *Int. J. Pept. Protein Res.*, Vol. 30, pp. 794-800 (1987); Barany, G., et al, "Solid-phase peptide Synthesis: A Silver Anniversary Report", *Int. J. Pept. Protein Res.*, Vol. 30, pp. 705-739 (1987), which are herein incorporated by reference). Specifically the 24-mer peptide of the invention described above is synthesized using an Applied Biosystems 430A Automated Synthesizer following the manufacturer's instructions. The synthetic peptide is cleaved from the resin and deblocked with hydrofluoric acid, using standard procedures described above, and the product is dialyzed, lyophilized and redissolved into appropriate buffers such as sodium phosphate or sodium chloride. Affinity purification involved passage of the crude peptide through calmodulin-agarose columns and elution with buffers containing EGTA in place of calcium as described in detail above.

Biochemical Data

The following examples further illustrate that the polypeptide compounds of the present invention are drugs capable of inhibiting calmodulin dependent biochemical pathways. A recent review by Hess and Colombani (*Prog. Allergy*, Vol. 38, pp.198-221 (1986)) which is herein incorporated by reference presents many examples of the good correlation that exists between in vitro activity of calmodulin binding compounds such as cyclosporin A and their in vivo activity as a potent immunesuppressive agents. Of course it is understood that the invention is not limited to the Examples described below.

EXAMPLE 4

Calmodulin dependent cAMP-phosphodiesterase (cAMP-PDE) Assay

A widely used criterion for establishing the identity of calmodulin binding molecules concerns their ability to inhibit the calmodulin dependent enzyme cAMP-phosphodiesterase. Procedures for evaluating the affinity of such compounds for calmodulin through this sensitive enzymatic assay are described in detail in Kincaid, R. L., et al., *Methods in Enzymology*, Vol. 159, pp. 457-470 (1988), which is herein incorporated by reference. The 24-mer described in the present invention is assessed for its ability to bind calmodulin, thereby inhibiting calmodulin dependent cAMP-PDE activity. Inhibition data indicates that the peptide has an apparent dissociation constant, KD, of 50 nM. This value is considerably lower than that observed for the binding of cyclosporin A to calmodulin (KD=0.1-6.0 uM) (Hess et al, *Prog. Allergy*, Vol. 38, pp. 198-221 (1986)). Thus, the peptide of the present invention may represent a more potent drug than cyclosporin A due to its higher affinity for calmodulin. This publication further shows that a good correlation exists between the in vivo activity of such calmodulin binding peptides and their ability to inhibit cAMP-PDE observed in vitro.

EXAMPLE 5

Fluorescence Spectral Assays

The 24-mer contains a single tryptophan residue which can serve as an intrinsic probe of the immediate environment of this peptide. The ultraviolet fluoroescence spectra exhibited by 0.5 uM aqueous solutions of the peptide (in the presence or absence of 0 5 uM $CaCl_2$) are indicative of tryptophan residues in a polar environment. The peptide is excited at a wavelength of 290 nm and exhibits an emission maximum at about 365 nm. Upon addition of calmodulin the emission spectra shows a dose dependent blue shift (wavelength max at 335 nm) and fluorescence yield enhancement ($\sim$2-fold). Saturation of binding is evident at a stoichiometry of 1 mole of calmodulin added per mole of peptide. Furthermore, calmodulin binding is evident by a dramatic relief in acrylamide (an aqueous collisional probe) induced fluorescence quenching. Both the calmodulin dependent fluoresence enhancement (and accompanied blue-shifting) as well as the quenching behavior are reversed by the addition of the calcium chelator EGTA, further illustrating the need for calcium for interaction between the 24-mer peptide and calmodulin. Flourescence assays have been employed to study the binding of Cyclosporin A to calmodulin (Hess et al, *Prog. Allergy* (1986) 38: 198-221), further illustrating the correlation between activity in such an in vitro assay and activity of such agents in vivo.

The peptides of the present invention are likely to affect a number of biochemical pathways that are mediated by fluctuations in intracellular calcium levels. Due to the critical role that changes in calcium levels play in cell activation, it is likely that these peptides could have widespread applications in the modulation of the biochemical state in many tissues or cell types.

The following are particular examples of other widely used drugs whose effects are known to be mediated through direct interactions with calmodulin, thereby altering the normal intracellulor responses to changes in calcium concentrations. Of course, it is understood that the invention is not limited to the applications described below.

EXAMPLE 6

Chlorpromazine and related phenathiazine compounds have been in wide use as sedative or antipsychotic agents since the 1950's. Trifluoroperizine, the best characterized of the phenothiazines, binds to calmodulin with an apparent dissociation constant, KD, of 5 uM. The drug binding sites have been mapped within hydrophobic surfaces which become available within the calcium bound form of calmodulin (Strynadka, N. C., et al *Proteins: Structure, Function and Genetics*, 1988, 3" 1–17. These same sites are thought to be essential in the association of calmodulin with spectrin, as well as a number of other enzymes that are regulated in a calcium/calmodulin dependent manner.

The polypeptide of the present invention is similarly believed to be useful as a sedative or anti-psychotic drug.

EXAMPLE 7

Cyclosporine A is a cyclic polypeptide consisting of 11 amino acids that is produced by the fungus species *Tolypocladium inflatum* Gams. The mechanism of this drug's action is thought to involve binding of the drug to calmodulin in T-lymphocyte resulting in the inhibition of release of factors that mediate immune reactions occurring during tissue graft rejection. Transplantation patients are usually maintained on the drug for life and must be carefully monitored for adverse toxic side effects.

The polypeptide of the present invention is similarly believed to be useful in mediating immune reactions occurring during tissue graft rejection.

The present invention is also directed to a method for treating various diseases or disorders which comprises administering to a human or animal (e.g., mammal or domestic animals such as, horses, pigs, cats, dogs) patient a pharmaceutically effective amount (e.g., 0.1-50 mg/kg/day) of the polypeptide of the present invention and a suitable carrier therefor.

The following disorders may be treated by the invention, including:

1. Prophylaxis against organ and tissue transplant rejection (kidney, heart, and liver transplants).
2. Treatment of autoimmune disorders.
3. Treatment of psychotic disorders such as schizophrenia, mania phase of manic depression.

The invention may also be used as a sedative (veterinary or human use).

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What we claim is:

1. An isolated polypeptide which consists essentially of the following sequence: Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu, a calmodulin binding active derivative thereof having said sequence as its nucleus, or a calmodulin binding active derivative having single or multiple amino acid substitutions, deletions or insertions and having the calmodulin binding activity of said sequence.

2. An isolated polypeptide which consists essentially of the following sequence: Pro-Trp-Lys-Ser-Ala-Arg-Leu-Met-Val-His-Thr-Val-Ala-Thr-Phe, a calmodulin binding active derivative thereof having said sequence as its nucleus, or a calmodulin binding active derivative having single or multiple amino acid substitutions, deletions or insertions and having the calmodulin binding activity of said sequence.

3. The polypeptide of claim 2, wherein contains 15–24 amino acid residues.

4. A composition comprising a therapeutically effective amount of the polypeptide of claim 1 for inhibiting biochemical activity linked to calmodulin and a pharmaceutically acceptable carrier therefor.

5. The composition of claim 4, which comprises 0.1 to 100% by weight of the polypeptide.

6. A sedative composition comprising the composition of claim 4.

7. A method for treating calmodulin related disorders which comprises administering to a patient a therapeutically effective amount of the composition of claim 4.

8. The method of claim 7, wherein the disorders include prophylaxis against organ and tissue transplant rejection.

9. The method of claim 7, wherein the disorder is an autoimmune disorder or a psychotic disorder.

10. The method of claim 7, wherein 0.1 to 50 mg/kg/day body weight of the composition is administered to the patient.

11. The method of claim 7, wherein the patient is a mammal.

12. The method of claim 11, wherein the patient is a human.

13. The method of claim 7, wherein the composition is orally administered or injected into a patient.

14. A pharmaceutical composition comprising a therapeutically effective amount of the polypeptide of claim 2 for inhibiting biochemical activity linked to calmodulin and a pharmaceutically acceptable carrier therefor.

15. The pharmaceutical composition of claim 4, wherein said polypeptide consists essentially of the following sequence:

Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu.

16. The pharmaceutical composition of claim 14, wherein said polypeptide consists essentially of the following sequence:

Pro-Trp-Lys-Ser-Ala-Arg-Leu-Met-Val-His-Thr-Val-Ala-Thr-Phe.

17. An isolated polypeptide which consists essentially of the following sequence: Pro-Trp-Lys-Ser-Ala-Arg-Leu-Met-Val-His-Thr-Val-Ala-Thr-Phe or a calmodulin binding active derivative thereof having said sequence as its nucleus.

18. An isolated polypeptide which consists essentially of the following sequence: Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu or a calmodulin binding acting derivative thereof having said sequence as its nucleus.

19. A pharmaceutical composition consisting essentially of a therapeutically effective amount of the polypeptide of claim 18 for inhibiting biochemical activity linked to calmodulin and a pharmaceutically acceptable carrier therefor.

20. A pharmaceutical composition of claim 19, which consists essentially of 0.1 to 100% by weight of the polypeptide.

21. A sedative composition which comprises the composition of claim 19.

22. A method for treating calmodulin related disorders which consists essentially of administering to a patient a therapeutically effective amount of the composition of claim 19.

23. The method of claim 22, wherein the disorders include prophylaxis against organ and tissue transplant rejection.

24. The method of claim 22, wherein the disorder is an autoimmune disorder or a psychotic disorder.

25. The method of claim 22, wherein 0.1 to 50 mg/kg/day body weight of the composition is administered to the patient.

26. The method of claim 22, wherein the patient is a mammal.

27. The method of claim 26, wherein the patient is a human.

28. The method of claim 22, wherein the composition is orally administered or injected into a patient.

29. The polypeptide of claim 17, which consists essentially of the following sequence:

Pro-Trp-Lys-Ser-Ala-Arg-Leu-Met-Val-His-Thr-Val-Ala-Thr-Phe.

30. The polypeptide of claim 18, which consists essentially of the following sequence:

Lys-Thr-Ala-Ser-Pro-Trp-Lys-Ser-Ala-Arg-Leu-Met-Val-His-Thr-Val-Ala-Thr-Phe-Asn-Ser-Ile-Lys-Glu.

* * * * *